(12) United States Patent
Souleiman et al.

(10) Patent No.: US 12,016,604 B2
(45) Date of Patent: Jun. 25, 2024

(54) METHODS AND DEVICES FOR ACHIEVING SEMI-RIGID BONE FIXATION

(71) Applicant: DePuy Synthes Products, Inc.

(72) Inventors: Firas Souleiman, Raynham, MA (US); Ivan Zderic, Raynham, MA (US); Torsten Pastor, Raynham, MA (US); Dominic Gehweiler, Raynham, MA (US); Boyko Gueorguiev-Rüegg, Raynham, MA (US); Michael Swords, Raynham, MA (US); Tim Schepers, Raynham, MA (US); Matthew Tomlinson, Raynham, MA (US); Charles Horrell, Raynham, MA (US); Nicholas Mourlas, Raynham, MA (US); Jon Thompson, Raynham, MA (US); Todd Kent, Raynham, MA (US); Jessica Galie, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/939,696

(22) Filed: Sep. 7, 2022

(65) Prior Publication Data
US 2024/0074868 A1     Mar. 7, 2024

(51) Int. Cl.
*A61B 17/86* (2006.01)
*A61B 17/88* (2006.01)
(Continued)

(52) U.S. Cl.
CPC ........ *A61B 17/8685* (2013.01); *A61B 17/863* (2013.01); *A61B 17/866* (2013.01);
(Continued)

(58) Field of Classification Search
CPC .............. A61B 17/863; A61B 17/8685; A61B 2017/564; A61B 2017/681
See application file for complete search history.

(56) References Cited

U.S. PATENT DOCUMENTS

| | | | |
|---|---|---|---|
| 5,306,290 | A | 4/1994 | Martins et al. |
| 7,235,091 | B2 | 6/2007 | Thornes |
| | | (Continued) | |

FOREIGN PATENT DOCUMENTS

| | | |
|---|---|---|
| CN | 108186096 A | 6/2018 |
| EP | 3 206 607 B1 | 5/2018 |
| RU | 2 461 366 C1 | 9/2012 |

OTHER PUBLICATIONS

Syndesmosis Tightrope XP Implant System, Arthrex Inc. (Year: 2019).*

*Primary Examiner* — Julianna N Harvey
(74) *Attorney, Agent, or Firm* — Troutman Pepper Hamilton Sanders LLP

(57) ABSTRACT

An example method is provided for maintaining stability to an injury defined by a separation of two bones (e.g., the tibia and fibula), the separation being an injured distance greater than a pre-injury distance between the two bones in a first human patient. The method may include delivering a first apparatus for approximation of the two bones in the first human patient comprising the injury, the first apparatus including a flexible segment disposed between a first anchor and a second anchor. The method may further include maintaining, by the first apparatus, a restored distance between the two bones in the first human patient after a repetitive dynamic loading, the restored distance approximately equal to the pre-injury distance.

19 Claims, 11 Drawing Sheets

(51) Int. Cl.
 *A61F 2/30* (2006.01)
 *A61F 2/42* (2006.01)
(52) U.S. Cl.
 CPC . *A61B 17/8866* (2013.01); *A61F 2002/30622* (2013.01); *A61F 2002/3085* (2013.01); *A61F 2/4202* (2013.01)

(56) References Cited

U.S. PATENT DOCUMENTS

| | | |
|---|---|---|
| 8,888,779 B2 | 11/2014 | Senn et al. |
| 9,421,049 B2 | 8/2016 | Rogachefsky |
| 9,737,347 B2 | 8/2017 | Schlienger et al. |
| 9,826,969 B2 | 11/2017 | Larsen |
| 10,327,826 B2 | 6/2019 | Horrell et al. |
| 10,492,774 B2 | 12/2019 | Larsen |
| 10,722,229 B2 | 7/2020 | O'Donnell et al. |
| 11,253,301 B2 | 2/2022 | Larsen et al. |
| 2012/0123474 A1* | 5/2012 | Zajac ............ A61B 17/0401 606/232 |
| 2016/0038186 A1 | 2/2016 | Herzog et al. |
| 2016/0287302 A1* | 10/2016 | Horrell ............ A61B 17/863 |
| 2018/0049784 A1 | 2/2018 | Gault et al. |
| 2022/0071676 A1 | 3/2022 | Horrell et al. |
| 2023/0390068 A1 | 12/2023 | Kent et al. |

\* cited by examiner

| | Number of Cycles (c) | | | | | |
|---|---|---|---|---|---|---|
| | 0c | 1000c | 2000c | 3000c | 4000c | 5000c |
| Magnitude Total Displacement Loaded (mm) | | | | | | |
| First Apparatus | 1.056 | 1.286 | 1.335 | 1.361 | 1.378 | 1.438 |
| Second Apparatus | 1.250 | 2.042 | 2.264 | 2.424 | 2.563 | 2.678 |

| Number of Cycles (c) | | | | | | |
|---|---|---|---|---|---|---|
| | 0c | 1000c | 2000c | 3000c | 4000c | 5000c |
| Amplitude Total Displacement (mm) | | | | | | |
| First Apparatus | 0.931 | 0.898 | 0.836 | 0.780 | 0.751 | 0.779 |
| Second Apparatus | 1.112 | 1.477 | 1.584 | 1.607 | 1.656 | 1.654 |

| | Number of Cycles (c) | | | | | |
|---|---|---|---|---|---|---|
| | 0c | 1000c | 2000c | 3000c | 4000c | 5000c |
| Magnitude AP Displacement (mm) | | | | | | |
| First Apparatus | 0.755 | 0.913 | 0.934 | 0.918 | 0.917 | 0.910 |
| Second Apparatus | 0.902 | 1.704 | 1.916 | 2.052 | 2.179 | 2.289 |

| | Number of Cycles (c) | | | | | |
|---|---|---|---|---|---|---|
| | 0c | 1000c | 2000c | 3000c | 4000c | 5000c |
| Amplitude AP Displacement (mm) | | | | | | |
| First Apparatus | 1.300 | 1.155 | 1.155 | 1.203 | 1.117 | 1.145 |
| Second Apparatus | 1.709 | 1.992 | 2.106 | 2.185 | 2.246 | 2.256 |

| Number of Cycles (c) | | | | | | |
|---|---|---|---|---|---|---|
| | 0c | 1000c | 2000c | 3000c | 4000c | 5000c |
| Magnitude Axial Displacement (mm) | | | | | | |
| First Apparatus | 0.521 | 0.466 | 0.468 | 0.477 | 0.480 | 0.492 |
| Second Apparatus | 0.533 | 0.892 | 0.970 | 1.037 | 1.091 | 1.156 |

METHODS AND DEVICES FOR ACHIEVING SEMI-RIGID BONE FIXATION

FIELD OF THE INVENTION

The present invention relates to apparatus and methods for semi-rigid fixation of bones. More specifically, certain embodiments relate to systems and methods for fixation of the distal tibia and distal fibula following an injury to the corresponding syndesmotic joint.

BACKGROUND

A syndesmotic injury results when a traumatic injury damages the ligaments that span the gap between the distal tibia and fibula. This can be the result of a high ankle sprain, with no fracture of the fibula, or can also accompany a fibular fracture in a Weber B or Weber C fracture.

A surgeon can determine the presence of a syndesmotic injury by direct visualization of the joint or through radiographic imaging while positioning the ankle in a mortise view orientation. In either case, loads are applied to the joint in either a direct lateral load applied to the fibula or by applying an external rotation load to the foot. While the load is being applied, the relative distance between the fibula and the tibia, the fibula and the talus, and the tibia and the talus are observed to determine the level of damage sustained by the ligaments that typically hold the syndesmotic joint together.

If a syndesmotic injury is found to be present, the typical treatment involves stabilizing the fibula and tibia with respect to each other in the proper orientation and holding them there throughout the soft tissue healing period to allow the ligaments to re-attach and heal. In the event of a syndesmotic injury with a corresponding fibula fracture, this is done while also stabilizing the fibular fracture, which is usually accomplished with a small fracture plate on the lateral side of the fibula. Traditionally the method of stabilization has been to place one or more cortical screws across the syndesmosis, with the head against the lateral face of the fibula and the tip of the screw being in the middle of the tibia or in the medial cortex of the tibia.

This form of treatment provides very rigid fixation, allowing the ligaments to heal, but makes return to weight-bearing more difficult. During a standard gait, the ligaments hold the distance between the tibia and fibula fairly constant, but allow a small amount of shear motion and rotation of the fibula with respect to the tibia. The presence of the fixation screws prevents this motion and can cause discomfort and limited flexibility of the ankle joint. Typically, the surgeon prescribes a secondary surgery to remove the screws once the ligaments have healed. In some cases, a surgeon may simply recommend a return to weight-bearing when the ligaments have healed and, after a period of time of loading the screws, they will experience a fatigue failure and normal anatomical motion will be restored.

To address these rigidity issues, some methods of stabilization have been developed to include a flexible internal segment connected by a first anchor on the lateral side of the fibula and a second anchor on the medial side of the tibia. These methods, however, require a through or bore hole through the medial wall of the tibia, which not only provides an additional point of necessary recovery, but also requires a physician to access a patient from multiple sides and angles during treatment.

In addition, some methods of stabilization including a flexible internal segment provide for inconsistencies in maintaining stability of the two bones following repair of a syndesmotic injury.

Accordingly, alternative apparatus and methods for providing semi-rigid fixation of the distal tibia and fibula following a syndesmotic injury would be useful.

SUMMARY

The present invention is directed to apparatus and methods for stabilizing a joint between two bones, e.g., the tibia and fibula, during the soft tissue healing period following a traumatic injury.

In an exemplary application, the apparatus and methods herein may be configured to provide substantially rigid tensile fixation between the tibia and fibula while allowing the small amount of shear and rotational motion required for a standard gait. This may make it possible for patients to return to weight-bearing earlier, which may improve clinical outcomes, and/or may also reduce the number of follow-up hardware-removal surgeries.

In some examples, a method is provided for maintaining stability to an injury defined by a separation of two bones (e.g., the tibia and fibula), the separation being an injured distance greater than a pre-injury distance between the two bones in a first human patient. The method may include delivering a first apparatus for maintaining the approximation of the two bones in the first human patient comprising the injury, the first apparatus including a flexible segment disposed between a first anchor and a second anchor. The method may further include maintaining, by the first apparatus, a restored distance between the two bones in the first human patient after a repetitive dynamic loading, the restored distance approximately equal to the pre-injury distance.

In some examples, delivering the first apparatus may further include maintaining the two bones to a repaired distance measured before the repetitive dynamic loading.

In some examples, the repetitive dynamic loading may cause axial translations of the two bones. The method may include maintaining, by the first apparatus, the axial translations of the two bones within a difference of approximately 5.57% from the repaired distance after 5000 repetitions. Maintaining of the axial translations may be conducted under a force of up to 1400 newtons (N). Maintaining of the axial translations may include a displacement equal to or less than about 0.1 mm.

In some examples, the repetitive dynamic loading may cause anterior to posterior, or anteroposterior, (AP) translations of the two bones. The method may include maintaining, by the first apparatus, the AP translations of the two bones within a difference of approximately 20.53% from the repaired distance after 5000 repetitions. Maintaining of the AP translations may be conducted under a force of up to 1400 N. Maintaining of the AP translations may include a displacement equal to or less than about 0.2 mm.

In some examples, the first anchor of the first apparatus may include a proximal end and a distal end configured for insertion into a first hole in a first bone of the two bones, where the first anchor may be configured such that there is a distance between the distal end of the first anchor and a medial side of the first bone. The second anchor of the first apparatus may include a proximal end and a distal end configured for insertion into a second hole in a second bone of the two bones. The flexible segment may extend between the first and second anchors limiting a spacing from the first anchor to the second anchor and may be configured to adjust a distance between the first and second bones.

In some examples, the method may include delivering a second apparatus for the approximation of the two bones in a second human patient, the second apparatus including a second flexible segment disposed between a third anchor and a fourth anchor. The method may include maintaining, by the second apparatus, the restored distance between the two bones in the second human patient after the repetitive dynamic loading, the restored distance approximately equal to the pre-injury distance. The method may include decreasing a first change in displacement of the two bones in the first human patient by the first apparatus compared to a second change in displacement of the two bones in the second human patient by the second apparatus.

In some examples, the repetitive dynamic loading may include axial translations of the two bones in the respective first and second human patients. The first change may include approximately 10.17% displacement, and the second change may include approximately 81.99% displacement, thereby decreasing, by the first apparatus, by at least 112.1% the displacement of the two bones in the first human patient after 2000 repetitions of axial translations. The first change may include approximately 5.57% displacement, and the second change may include approximately 116.89% displacement, thereby decreasing, by the first apparatus, by at least 104.7%, the displacement of the two bones in the first human patient after 5000 repetitions of axial translations.

In some examples, the repetitive dynamic loading may include AP translations of the two bones in the respective first and second human patients. The first change may include approximately 23.71% displacement, and the second change may include approximately 112.42% displacement, thereby decreasing, by the first apparatus, by at least 82.3%, the displacement of the two bones in the first human patient after 2000 repetitions of AP translations. The first change may include approximately 20.53% displacement, and the second change may include approximately 153.77% displacement, thereby decreasing, by the first apparatus, by at least 88.8%, the displacement of the two bones in the first human patient after 5000 repetitions of AP translations.

In some examples, a method is provided for maintaining stability to an injury defined by a separation of two bones (e.g., the tibia and fibula), the separation being an injured distance greater than a pre-injury distance between the two bones in a first human patient. The method may include delivering a first apparatus for approximation of the two bones in the first human patient comprising the injury, and maintaining, by the first apparatus, a restored distance between the two bones after a repetitive dynamic loading, the restored distance approximately equal to the pre-injury distance. The first apparatus may include a first anchor configured such that there is a distance between a distal end of the first anchor and a medial side of a first bone of the two bones, a second anchor configured for insertion into a second bone of the two bones, and a flexible segment extending between the first and second anchors and configured to adjust a distance between the first and second bones.

In some examples, a method is provided for maintaining stability to an injury defined by a separation of two bones (e.g., the tibia and fibula), the separation being an injured distance greater than a pre-injury distance between the two bones in a first human patient. The method may include delivering a first apparatus for approximation of the two bones in the first human patient comprising the injury, the first apparatus including a flexible segment disposed between a first anchor and a second anchor. The method may include executing a repetitive dynamic loading of the two bones, the repetitive dynamic loading causing axial translations of the two bones. The method may include maintaining, by the first apparatus, a restored distance between the two bones after the repetitive dynamic loading, the restored distance approximately equal to the pre-injury distance.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Figure 1:
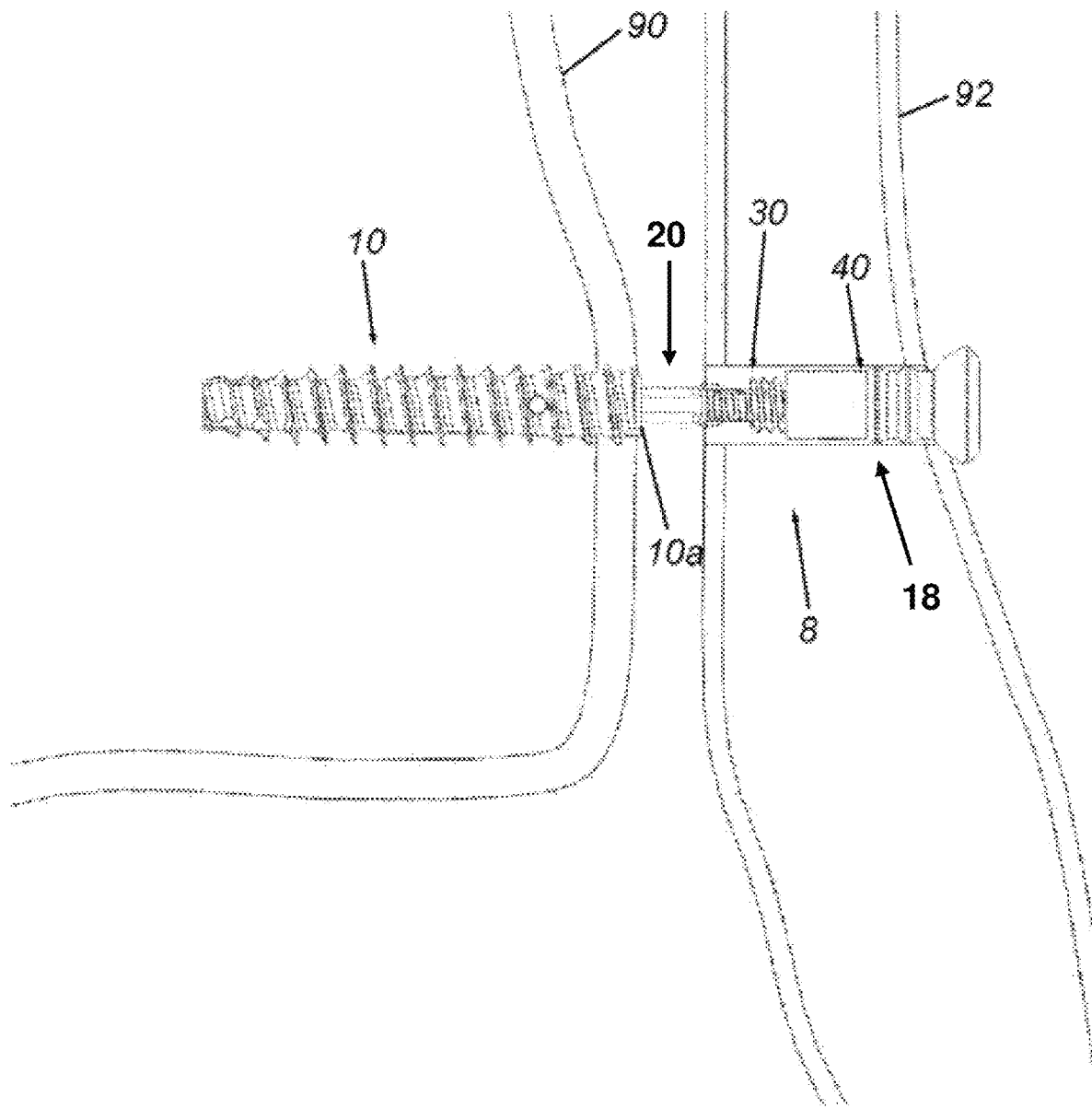
FIG. 1 is a mortise view of an exemplary embodiment of an apparatus for providing semi-rigid fixation between two bones, according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

As used herein, the term "clear space" may indicate a distance or gap between two bones (e.g., the tibia and fibula) at any point in time pre- or post-syndesmotic injury to the two bones.

As used herein, the term "pre-injury" or "pre-injury distance" may indicate a distance or gap between two bones (e.g., the tibia and fibula) prior to a syndesmotic injury to the two bones.

As used herein, the term "injured" or "injured distance" may indicate a distance or gap between two bones (e.g., the tibia and fibula) immediately following a syndesmotic injury to the two bones, e.g., a dissection of ligaments contained therein.

As used herein, the term "repaired" or "repaired distance" may indicate a distance or gap between two bones (e.g., the tibia and fibula) immediately following surgery to the two bones to repair a syndesmotic injury to the two bones. As used herein, the term "surgery" may indicate repairing a syndesmotic injury to the two bones in one or more cadaver samples.

As used herein, the term "restored" or "restored distance" may indicate a distance or gap between two bones (e.g., the tibia and fibula) after testing the repaired bones under repetitive dynamic loading (e.g., axial movements, and/or AP movements).

The example devices and methods of treatment described herein may generally involve providing semi-rigid fixation of two bones, such as the tibia and fibula bones, by implanting an apparatus, for example, including a first anchor, a second anchor, and a flexible segment, through the fibula bone and into only one side of the tibia bone. That is, the disclosed example devices and methods of treatment may not require a second hole be made through the medial wall of the tibia bone. Instead, an apparatus can be inserted through the fibula bone and only partially into the tibia bone. The disclosed example devices and methods of treatment may thus prevent an additional point of necessary patient recovery.

The example devices and methods of treatment described herein may further involve comparing a first apparatus, such as the apparatus described above, to a second apparatus, in maintaining stability in two bones (e.g., the tibia and fibula) following a syndesmotic injury to the two bones when the two bones are placed under repetitive dynamic loading, as further discussed herein.

Various example systems and methods are presented herein. Features from each example are combinable with other examples as understood by persons skilled in the pertinent art.

Study Overview

A primary objective of the study was to compare the stabilization of a joint between two bones (e.g., the tibia and fibula) among subjects undergoing fixation for ankle syndesmosis with a form of a fixation apparatus, which can include a screw-suture system 8 (FIBULINK® Syndesmosis Repair System, DEPUY SYNTHES, Raynham, MA), which is subject of U.S. patent application Ser. Nos. 17/526,926, and 17/831,565, the entire contents of each of which are fully incorporated herein by reference.

Figure 2:
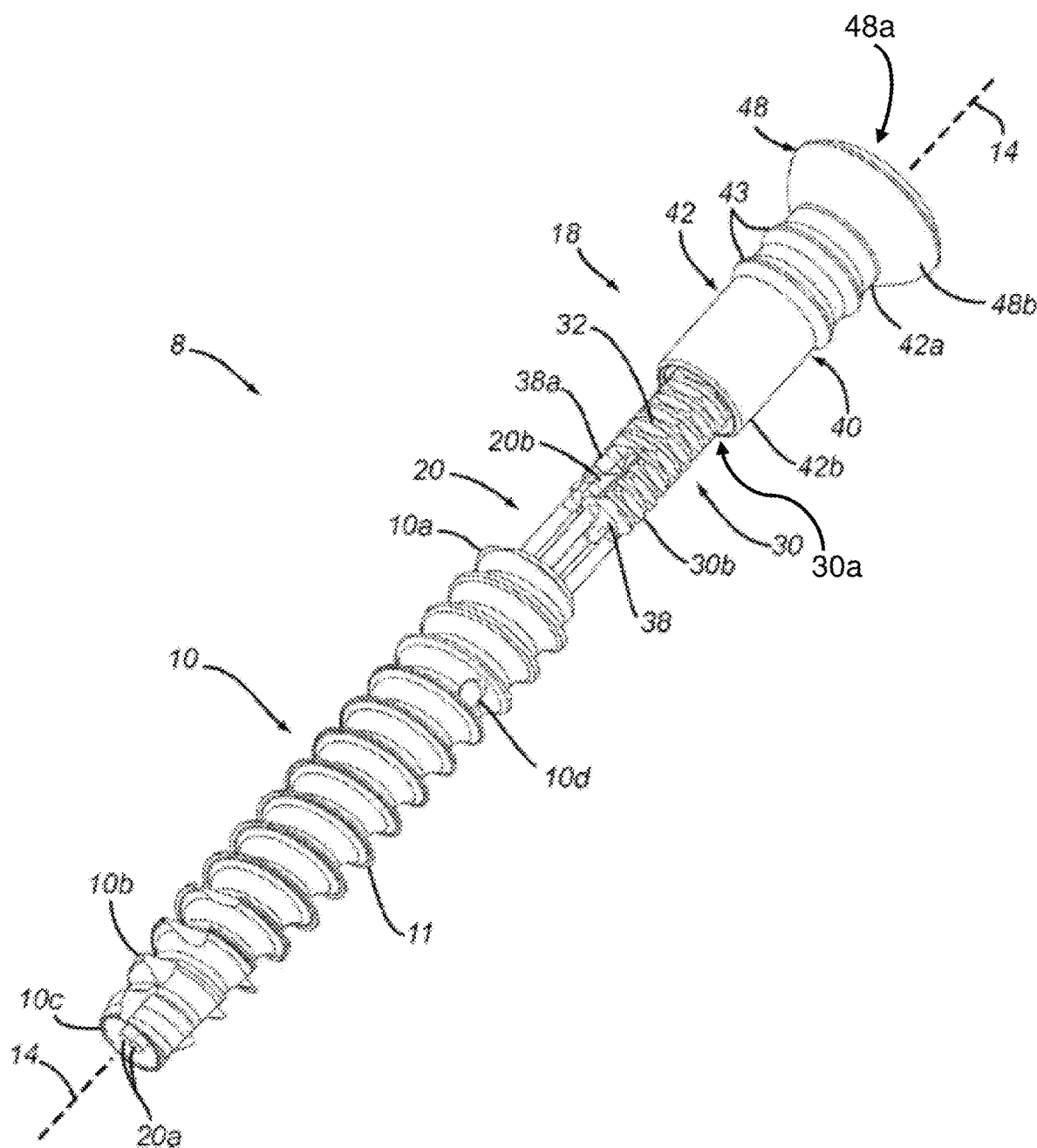
FIG. 2 is a perspective view of the apparatus of FIG. 1, according to aspects of the present invention.

Turning to the drawings, FIGS. 1 and 2 show an exemplary embodiment of screw-suture system or apparatus 8 for providing semi-rigid fixation between two bones that generally may include a first anchor 10 configured for insertion into a first bone, e.g., a tibia 90 (shown in FIG. 1), a second anchor 18 for engaging a second bone adjacent the first bone, e.g., a fibula 92 (shown in FIG. 1), and a flexible segment 20 extending between the first and second anchors 10, 18, e.g., to provide approximation between the first and second bones 90, 92. The second anchor 18 may generally include a first or distal component 30 coupled to the first anchor 10 by the flexible segment 20 and a second or proximal component 40 configured to be threaded over the first component 30 for engaging the second bone 92.

As particularly shown in FIG. 2, the first anchor 10 may be a rigid elongate member including a proximal end 10a, a distal end 10b configured for insertion into a first bone and terminating at a distal tip 10c, one or more external threads 11 extending at least partially between the proximal and distal ends 10a, 10b, and a bore (not shown) extending from the proximal end 10a at least partially towards the distal end 10b, generally along a longitudinal axis 14 of the apparatus 8.

The external threads 11 may extend from the proximal end 10a helically towards the distal end 10b, e.g., entirely to the distal tip 10c or the threads 11 may terminate before the distal tip 10c, e.g., to provide a smooth-walled, unthreaded distal tip (not shown). The threads 11 may have a substantially uniform configuration along the threaded region of the first anchor 10 or the threads 11 may be varied as desired, e.g., having different heights, edges, and/or axial spacing (threads per millimeter), as desired.

Optionally, the threads 11 may end before the proximal-most edge of the first anchor 10, e.g., about half to one millimeter (0.5-1.0 mm). Such an offset may facilitate identifying the end of the first anchor 10, e.g., to identify the interface between the first anchor 10 and an apparatus delivery tool (not shown). In addition, the offset may provide an unthreaded region on the proximal end 10a in case the first anchor 10 extends a small distance from a bone into which it is implanted, which may reduce risk of irritation and/or damage to adjacent tissue.

With continued reference to FIGS. 1 and 2, the first component 30 of the second anchor 18 may be an elongate rod or tubular body including a proximal end 30a, a distal end 30b, and one or more external threads 32 extending at least partially between the proximal and distal ends 30a, 30b. In addition, the first component 30 may have an outer profile to facilitate coupling the first component 30 between the apparatus delivery tool (not shown) and the first anchor 10. For example, as best seen in FIG. 2, the first component 30 may have a substantially uniform hexagonal outer profile along its length with the threads 32 conforming to the outer profile. The outer profile may generally correspond to the size and shape of the proximal region of the bore (not shown) in the first anchor 10, thereby allowing the distal end 30b of the first component 30 to be inserted into the proximal region of the bore. Similarly, the proximal end 30a may have an outer profile corresponding to a lumen, recess, or other passage in the apparatus delivery tool such that the proximal end 30a may be inserted into the apparatus delivery tool, thereby causing the first component 30 to transfer torque from the apparatus delivery tool to the first anchor 10. It will be appreciated that the proximal and distal ends 30a, 30b may have similar profiles (e.g., the first component 30 may have a substantially uniform shape along its length), or the proximal and distal ends 30a, 30b may have different shapes and/or sizes as long as they correspond to the size and shape of the sockets in the first anchor 10 and apparatus delivery tool that receive them.

In addition, the first component 30 may include a second mount or support structure 38, e.g., adjacent the distal end 30b for coupling the flexible segment 20 to the first component 30. In the exemplary embodiment shown, an aperture or passage 38a is provided that extends through the first component 30 adjacent the distal end 30b, e.g., through opposite side walls thereof substantially perpendicular to the longitudinal axis 14. The passage 38a may have rounded surfaces and the like to accommodate wrapping a portion of the flexible segment 20 through the passage 38a and at least partially around the second mount 38.

In an exemplary embodiment, the flexible segment 20 may be an elongate length of suture or other filament having first and second ends 20a (FIG. 2). During assembly, one of the ends 20a may be directed through the passage 38a until a central region 20b is disposed around the second mount 38, thereby defining a loop. The ends 20a may then be directed into the bore of the first anchor 10 until the ends 20a exit the bore and distal tip 10c. The ends 20a may then be secured together, e.g., by tying one or more knots having a cross-section configured to prevent the ends 20a from being pulled back through the bore (not shown) of the first anchor 10 during implantation. It will be appreciated that alternative methods for securing the ends 20a may be used.

The ends 20a may also be tied or secured to provide a predetermined length of flexible segment 20, thereby providing a desired maximum spacing between the first anchor 10 and the first component 30 of the second anchor 18. For example, the length of the flexible segment 20 may be set such that the maximum spacing between the proximal end 10a of the first anchor 10 and the distal end 30b of the first component 30 may be between about two and four millimeters (2-4 mm). It will be appreciated that other configurations may be provided for the flexible segment 20 to flexibly connect the first anchor 10 and the first component 30.

With continued reference to FIGS. 1 and 2, the second component 40 of the second anchor 18 may generally include an elongate tubular body 42 including a proximal end 42a, a distal end 42b, and an internal passage (not shown) extending at least partially from the distal end 42b towards the proximal end 42a. The internal passage may be sized to be advanced over the proximal end 30a of the first component 30 and includes one or more internal threads (not shown) for cooperating with the external threads 32 on the first component 30, e.g., to allow the second component 40 to be controllably advanced over the first component 30.

In addition, the second component 40 may include an enlarged head 48 on the proximal end 42a, e.g., including a substantially flat or otherwise shaped proximal surface 48a and a flared or other expanding distal surface 48b, e.g. for engaging the second bone 92 as shown in FIG. 1.

Optionally, the tubular body 42 may include one or more annular ridges or other features 43 on an outer surface of the tubular body 42, e.g., adjacent the proximal end 42a. For example, the tubular body 42 may have an outer diameter smaller than a clearance hole drilled in bone through which the second component 40 is introduced, and the annular ridges 43 may have a diameter similar to the clearance hole such that ridges 43 may contact surrounding bone to secure the tubular body 42 within the bone, e.g., once bony ingrowth occurs.

To study the treatment of acute distal tibiofibular syndesmotic disruptions, the disclosed study compared the above-described apparatus 8, hereinafter "first apparatus 8," and a second apparatus including a screwless fixation system (Syndesmosis TIGHTROPE® XP Implant System, ARTHREX, Naples, FL), in maintaining stability between the tibia and fibula bones following syndesmotic injury. The second apparatus comprises two opposing buttons (e.g., stainless steel or titanium) and two suture strands of Fiber-Wire suture. The second apparatus uses bone-to-bone fixation, with the opposing buttons abutting the medial side of the first bone and a lateral side of the second bone, respectively, such that the suture strands extend between the two buttons to approximate the two bones.

In one study, eight pairs of human cadaveric lower legs were CT scanned under 700 N single-leg axial loading in five foot positions: (1) neutral, (2) 15° external rotation, (3) 15° internal rotation, (4) 20° dorsiflexion, and (5) 20° plantarflexion. Each pair of legs was CT scanned in three different states: (1) pre-injury; (2) injured, characterized by complete syndesmosis and deltoid ligaments cuts simulating pronation-eversion injury types III and IV as well as supination-eversion injury type IV according to Lauge-Hansen; and (3) repaired, using the first apparatus 8 or the second apparatus for syndesmotic stabilization, placed 20 mm proximal to the tibia plafond/joint surface. Following, all specimens were: (1) biomechanically tested over 5000 cycles under combined 1400 N axial and ±15° torsional loading; and (2) rescanned. Clear space (diastasis), anterior tibiofibular distance, talar dome angle, and fibular shortening were measured radiologically from CT scans. Anteroposterior, axial, mediolateral, and torsional movements at the distal tibiofibular joint level were evaluated biomechanically via motion tracking.

Figure 3A:
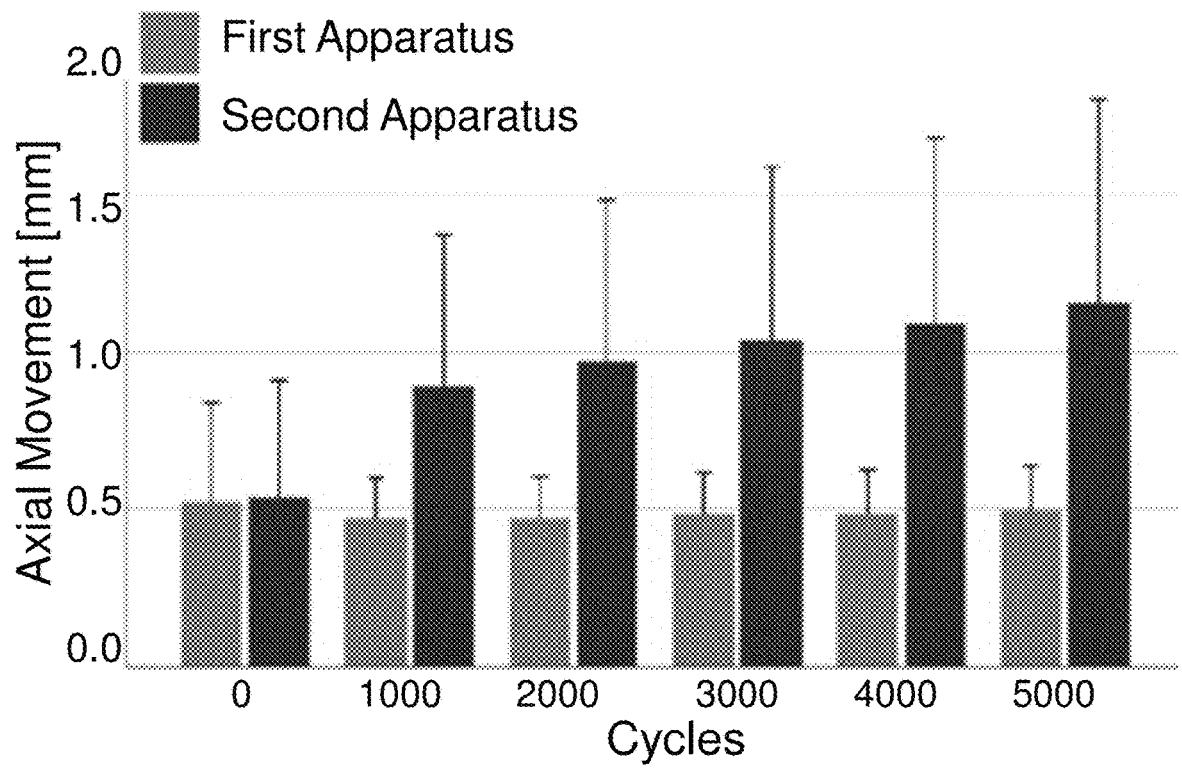
FIG. 3A is a graphical summary comparing stability between two bones maintained by another apparatus with the apparatus of FIG. 1 from a study of this disclosure.
Figure 3B:
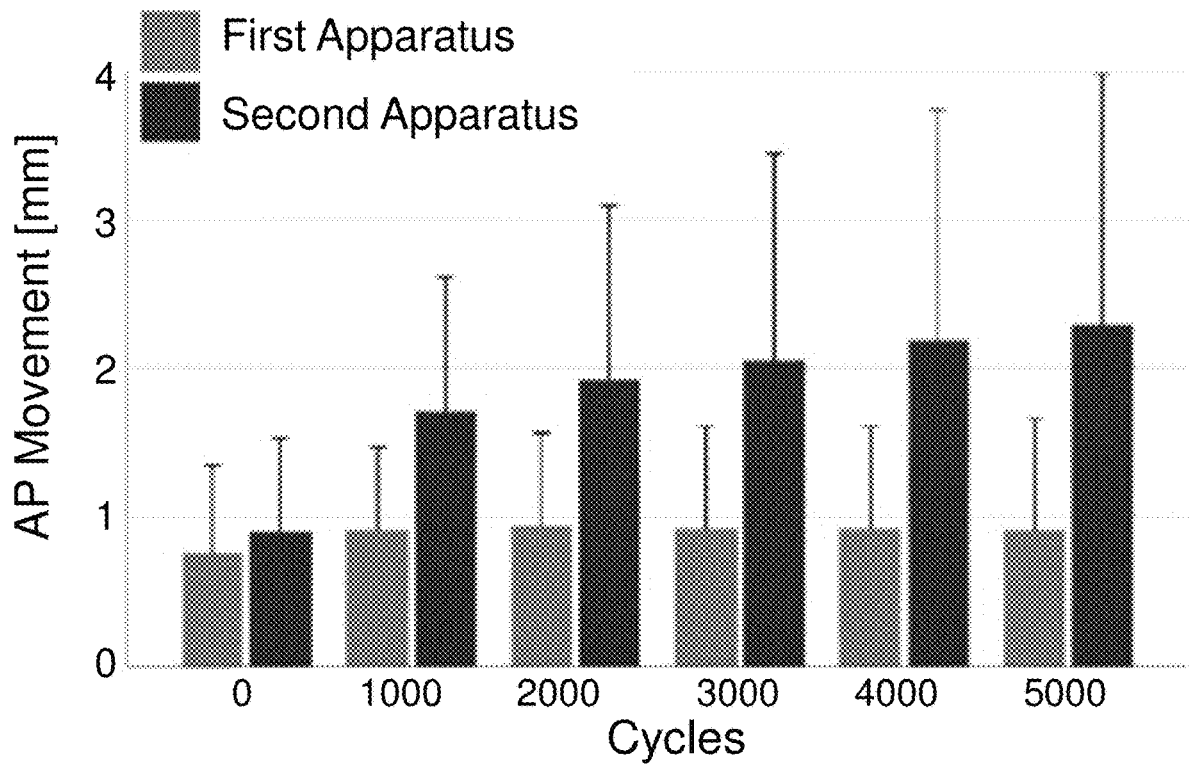
FIG. 3B is a graphical summary comparing stability between two bones maintained by another apparatus with the apparatus of FIG. 1 from a study of this disclosure.

The results of such study are provided in FIGS. 3A-3B. FIG. 3A provides a comparison between the first and second apparatus in maintaining stability between the repaired bones upon axial movement of the specimens. The axial movement (mm) was recorded at 0 cycles (immediately following repair), 1000 cycles, 2000 cycles, 3000 cycles, 4000 cycles, and 5000 cycles. FIG. 3B provides a comparison between the first and second apparatus in maintaining stability between the repaired bones upon AP movement of the specimens. The AP movement (mm) was also recorded at 0 cycles (immediately following repair), 1000 cycles, 2000 cycles, 3000 cycles, 4000 cycles, and 5000 cycles.

With respect to both the first and second apparatus, clear space in the specimens increased significantly after injury ($p \leq 0.004$) and became significantly smaller in the repaired specimens compared with both the pre-injured and injured states ($p \leq 0.041$). Anteroposterior and axial movements were significantly smaller in Group 1 compared with Group 2 ($p < 0.001$).

Accordingly, the study showed that although both apparatuses (Group 1 and Group 2) demonstrate ability for stabilization of unstable syndesmotic injuries, the screw-suture reconstruction (first apparatus 8) provides better AP translation and axial stability of the tibiofibular joint and maintains it over time under dynamic loading. Therefore, it could be considered as a valid option for treatment of syndesmotic disruptions.

In another study, eight pairs of human cadaveric lower legs with pes planovalgus were acquired. A complete delta cut was made in each specimen, resulting in dislocations of the tibia over the talus, followed by two fibula fractures. The specimens were CT scanned under two loading states: 75 N unloaded and 700 N loading, and in five foot positions: (1) neutral, (2) 15° external rotation, (3) 15° internal rotation, (4) 20° dorsiflexion, and (5) 20° plantarflexion. Peak compression (1400 N~2×BW) was applied in phase with 15° peak external foot rotation. Valley compression (50 N) was applied with 15° peak internal foot rotation. The legs were also CT scanned in three different states: (1) pre-injury; (2) injured, characterized by complete syndesmosis and deltoid ligaments cuts simulating pronation-eversion injury types III and IV as well as supination-eversion injury type IV according to Lauge-Hansen; and (3) repaired, and using the first apparatus 8 or the second apparatus (a suture-button repair device) implants for syndesmotic stabilization, placed 20 mm proximal to the tibia plafond/joint surface. Following, all specimens were: (1) biomechanically tested over 5000 cycles under combined 1400 N axial and ±15° torsional loading; and (2) rescanned. Clear space (diastasis), anterior tibiofibular distance, talar dome angle, and fibular shortening were measured radioloxlly from CT scans. Anteroposterior, axial, mediolateral, and torsional movements at the distal tibiofibular joint level were evaluated biomechanically via motion tracking. The results of such study are provided in FIGS. 4A-4B, 5A-5B, 6A-6B, 7A-7B, 8A-8B, and 9A-9B.

Figures 4A, 4B:
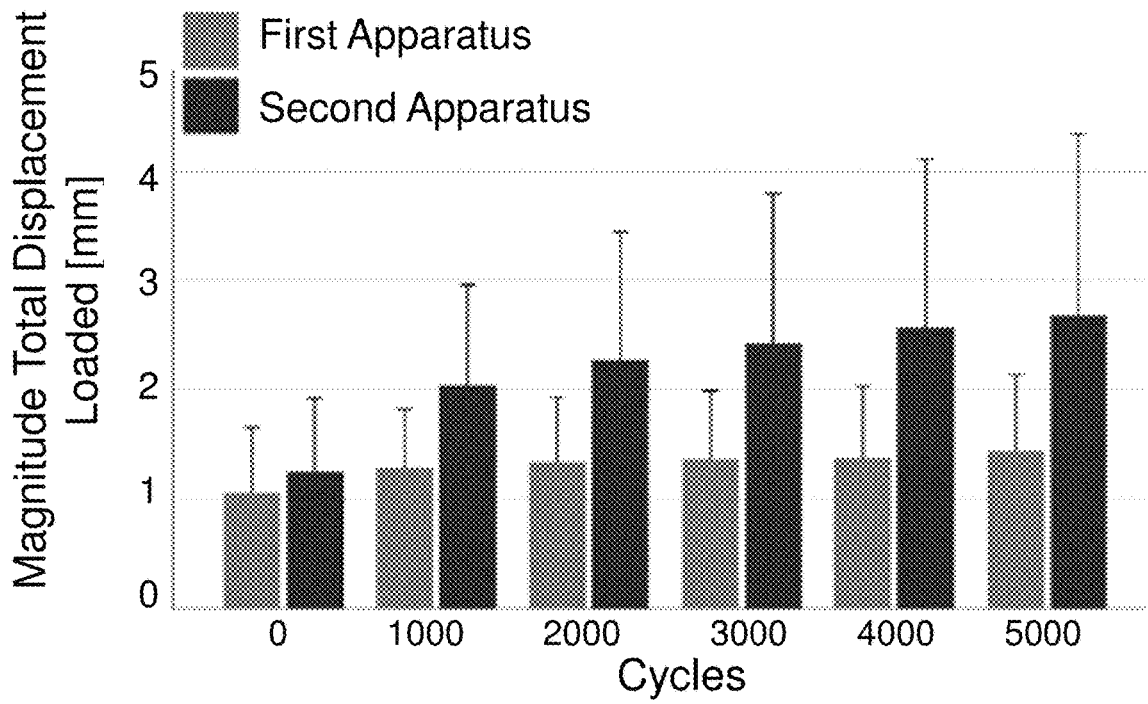
FIG. 4A is a graphical summary comparing stability between two bones maintained by another apparatus with the apparatus of FIG. 1 from a study of this disclosure.
FIG. 4B is a table summarizing the data from the graphical summary of FIG. 4A.

FIG. 4A provides a comparison in stability between the tibia and fibula bones maintained by the first apparatus 8 and the second apparatus. FIG. 4B provides a table summarizing the data included in FIG. 4A. Magnitude of total displacement (mm) in the studied specimens was measured under peak loading of up to 1400 N at 0 cycles (immediately following repair), 1000 cycles, 2000 cycles, 3000 cycles, 4000 cycles, and 5000 cycles. As shown in FIGS. 4A-4B, a significant difference was found between Group 1 and Group 2 (p=0.027).

Figures 5A, 5B:
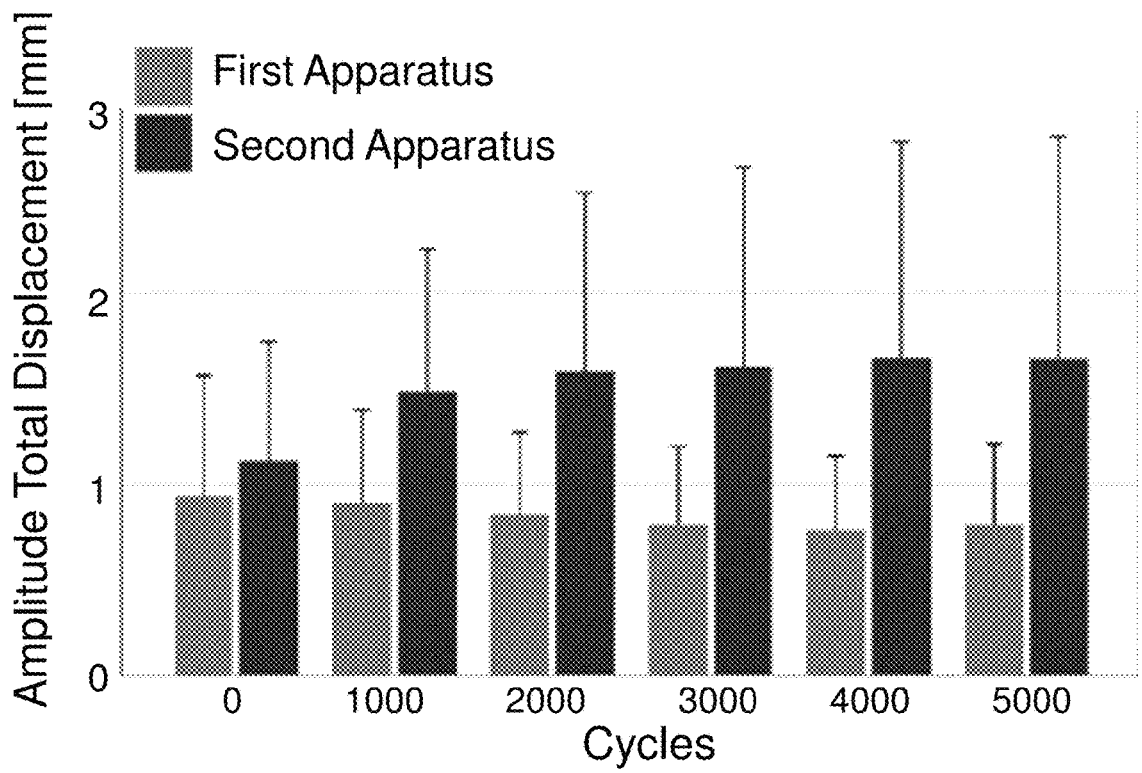
FIG. 5A is a graphical summary comparing stability between two bones maintained by another apparatus with the apparatus of FIG. 1 from a study of this disclosure.
FIG. 5B is a table summarizing the data from the graphical summary of FIG. 5A.

FIG. 5A provides a comparison in stability between the tibia and fibula bones maintained by the first apparatus 8 and the second apparatus. FIG. 5B provides a table summarizing the data included in FIG. 5A. Amplitude of total displacement (mm) in the studied specimens was measured between peak and valley loading at 0 cycles (immediately following repair), 1000 cycles, 2000 cycles, 3000 cycles, 4000 cycles, and 5000 cycles. As shown in FIGS. 5A-5B, a significant difference was found between Group 1 and Group 2 (p=0.019).

Figures 6A, 6B:
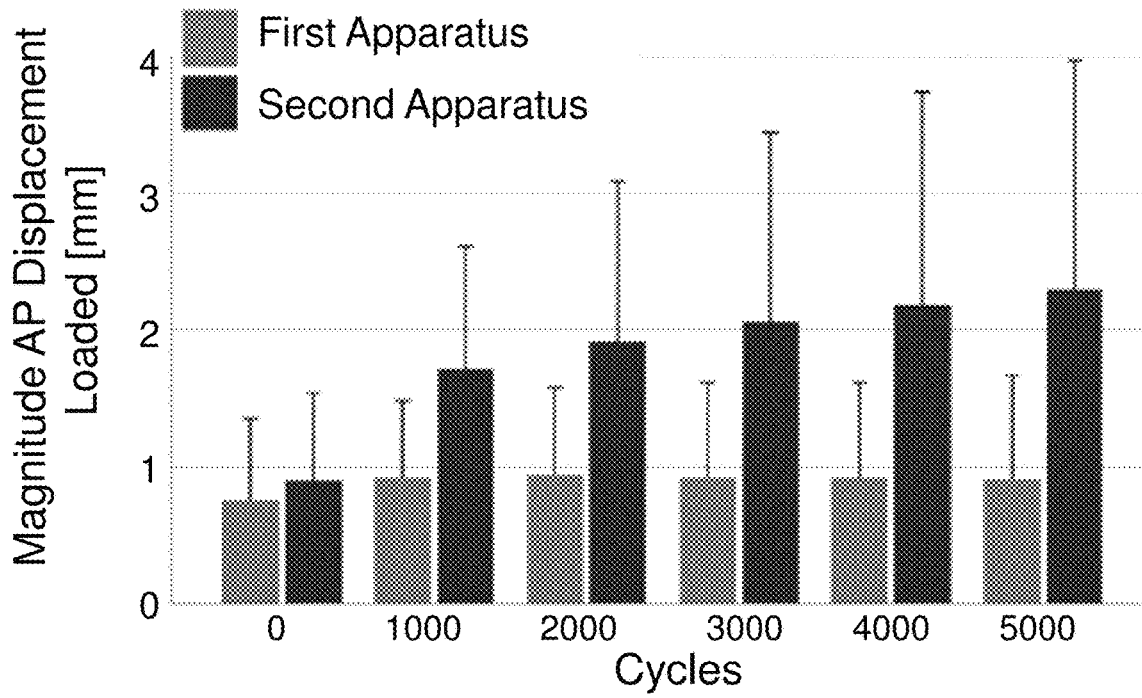
FIG. 6A is a graphical summary comparing stability between two bones maintained by another apparatus with the apparatus of FIG. 1 from a study of this disclosure.
FIG. 6B is a table summarizing the data from the graphical summary of FIG. 6A.

FIG. 6A provides a comparison in stability between the tibia and fibula bones maintained by the first apparatus 8 and the second apparatus. FIG. 6B provides a table summarizing the data included in FIG. 6A. Magnitude of AP displacement (mm) in the studied specimens was measured under peak loading of up to 1400 N at 0 cycles (immediately following repair), 1000 cycles, 2000 cycles, 3000 cycles, 4000 cycles, and 5000 cycles. As shown in FIGS. 6A-6B, a significant difference was found between Group 1 and Group 2 (p<0.001).

As shown in FIGS. 6A-6B, the first apparatus 8 maintained the AP displacement of the tibia and fibula bones within a difference of approximately 20.93% (abs(0.913−0.755)/0.755) from the repaired distance (at 0 cycles) after 1000 cycles or repetitions, while the second apparatus maintained the AP displacement of the two bones within a difference of approximately 88.91% (abs(1.704−0.902)/0.902). The first apparatus 8 also maintained the AP displacement of the tibia and fibula bones equal to or less than about 0.2 mm, or equal to or less than about 0.158 mm (abs(0.913−0.755)), after 1000 cycles, while the second apparatus maintained the AP displacement of the two bones equal to or less than about 0.802 mm (abs(1.704−0.902)). These data points reveal that, compared to the second apparatus, the first apparatus 8 decreased the AP displacement of the two bones by about 80.3% after 1000 cycles (abs(0.802−0.158)/0.802)).

As further shown in FIGS. 6A-6B, the first apparatus 8 maintained the AP displacement of the tibia and fibula bones within a difference of approximately 23.71% from the repaired distance after 2000 cycles, while the second apparatus maintained the AP displacement of the two bones within a difference of approximately 112.42%. The first apparatus 8 also maintained the AP displacement of the two bones equal to or less than about 0.2 mm, or equal to or less than about 0.179 mm, after 2000 cycles, while the second apparatus maintained the AP displacement of the two bones equal to or less than about 1.014 mm. These data points reveal that, compared to the second apparatus, the first apparatus 8 decreased the AP displacement of the two bones by about 82.3% after 2000 cycles.

As further shown in FIGS. 6A-6B, the first apparatus 8 maintained the AP displacement of the tibia and fibula bones within a difference of approximately 20.53% from the repaired distance after 5000 cycles, while the second apparatus maintained the AP displacement of the two bones within a difference of approximately 153.77%. The first apparatus 8 also maintained the AP displacement of the two bones equal to or less than about 0.2 mm, or equal to or less than about 0.155 mm, after 5000 cycles, while the second apparatus maintained the AP displacement of the two bones equal to or less than about 1.387 mm. These data points reveal that, compared to the second apparatus, the first apparatus 8 decreased the AP displacement of the two bones by about 88.8% after 5000 cycles.

Figures 7A, 7B:
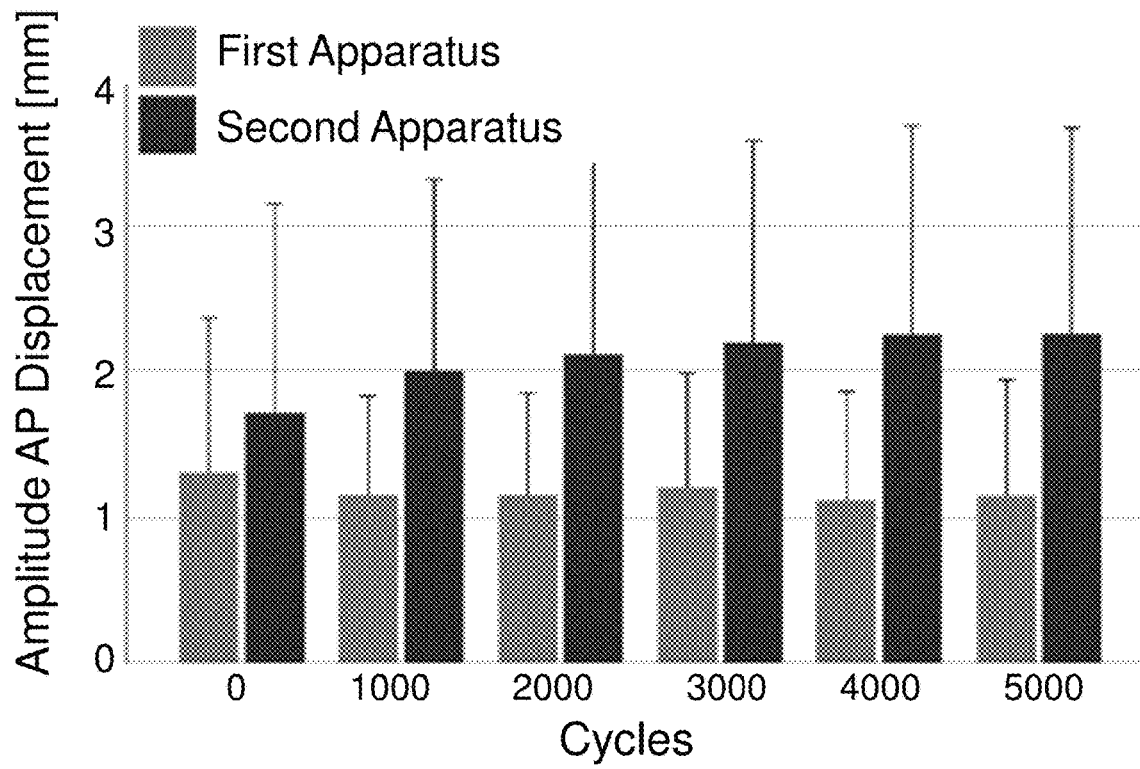
FIG. 7A is a graphical summary comparing stability between two bones maintained by another apparatus with the apparatus of FIG. 1 from a study of this disclosure.
FIG. 7B is a table summarizing the data from the graphical summary of FIG. 7A.

FIG. 7A provides a comparison in stability between the tibia and fibula bones maintained by the first apparatus 8 and the second apparatus. FIG. 7B provides a table summarizing the data included in FIG. 7A. Amplitude of AP displacement (mm) in the studied specimens was measured between peak and valley loading at 0 cycles (immediately following repair), 1000 cycles, 2000 cycles, 3000 cycles, 4000 cycles, and 5000 cycles. As shown in FIGS. 7A-7B, a significant difference was found between Group 1 and Group 2 (p<0.001).

Figures 8A, 8B:
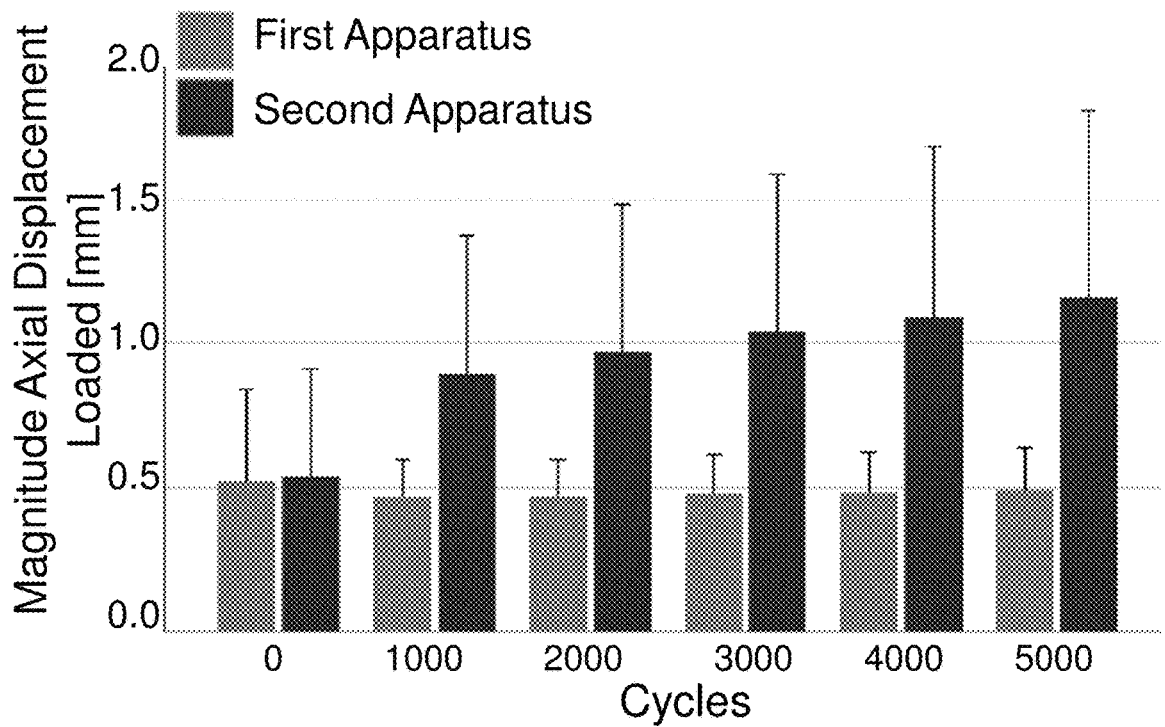
FIG. 8A is a graphical summary comparing stability between two bones maintained by another apparatus with the apparatus of FIG. 1 from a study of this disclosure.
FIG. 8B is a table summarizing the data from the graphical summary of FIG. 8A.

FIG. 8A provides a comparison in stability between the tibia and fibula bones maintained by the first apparatus 8 and the second apparatus. FIG. 8B provides a table summarizing the data included in FIG. 8A. Magnitude of axial displacement (mm) in the studied specimens was measured under peak loading of up to 1400 N at 0 cycles (immediately following repair), 1000 cycles, 2000 cycles, 3000 cycles, 4000 cycles, and 5000 cycles. As shown in FIGS. 8A-8B, a significant difference was found between Group 1 and Group 2 (p<0.001).

As shown in FIGS. 8A-8B, the first apparatus 8 maintained the axial displacement of the tibia and fibula bones within a difference of approximately 10.56% (abs(0.466−0.521)/0.521) from the repaired distance (at 0 cycles) after 1000 cycles or repetitions, while the second apparatus maintained the axial displacement of the two bones within a difference of approximately 67.35%. The first apparatus 8 also maintained the axial displacement of the two bones equal to or less than about 0.1 mm, or equal to or less than 0.055 mm (abs(0.466−0.521)), after 1000 cycles, while the second apparatus maintained the axial displacement of the two bones equal to or less than about 0.359 mm. These data points reveal that, compared to the second apparatus, the first apparatus 8 decreased the axial displacement of the two bones by about 115.3% after 1000 cycles.

As further shown in FIGS. 8A-8B, the first apparatus 8 maintained the axial displacement of the tibia and fibula bones within a difference of approximately 10.17% from the repaired distance after 2000 cycles, while the second apparatus maintained the axial displacement of the two bones within a difference of approximately 81.99%. The first apparatus 8 also maintained the axial displacement of the two bones equal to or less than about 0.1 mm, or equal to or less than about 0.053 mm, after 2000 cycles, while the second apparatus maintained the axial displacement of the two bones equal to or less than about 0.437 mm. These data points reveal that, compared to the second apparatus, the first apparatus 8 decreased the axial displacement of the two bones by about 112.1% after 2000 cycles.

As further shown in FIGS. 8A-8B, the first apparatus 8 maintained the axial displacement of the tibia and fibula bones within a difference of approximately 5.57% from the repaired distance after 5000 cycles, while the second apparatus maintained the axial displacement of the two bones within a difference of approximately 116.89%. The first apparatus 8 also maintained the axial displacement of the two bones equal to or less than about 0.1 mm, or equal to or less than about 0.029 mm, after 5000 cycles, while the second apparatus maintained the axial displacement of the two bones equal to or less than about 0.623 mm. These data points reveal that, compared to the second apparatus, the first apparatus 8 decreased the axial displacement of the two bones by about 104.7% after 5000 cycles.

Accordingly, the study showed that while both the first and second apparatus demonstrated over-compression and less clear space after repair compared to the pre-injury state, in the specimens including the first apparatus 8, over-compression was neutralized after biomechanical testing. Finally, the study showed that the first apparatus 8 was significantly more stable with respect to axial and AP fibula movements compared to the second apparatus.

Figure 9:
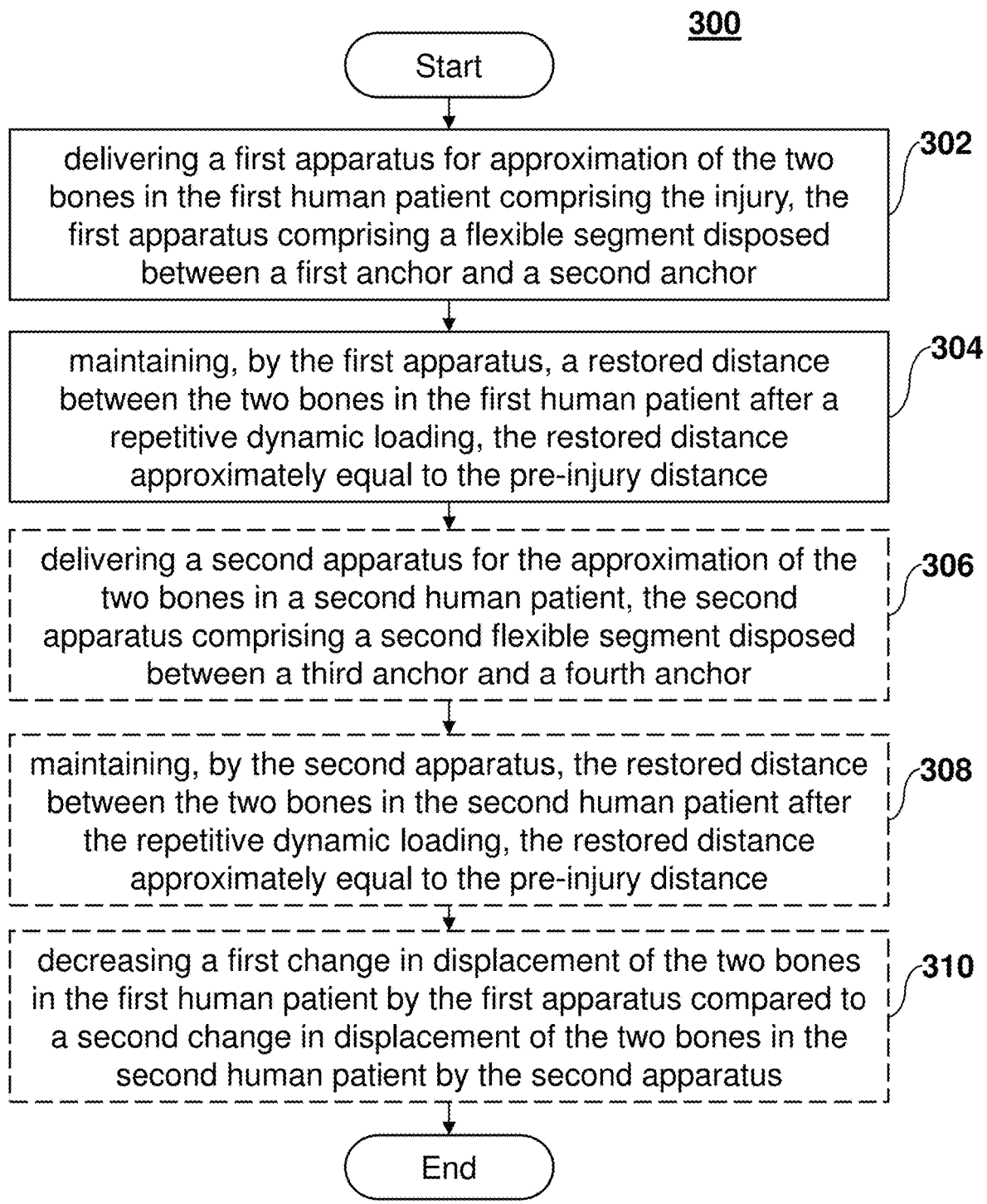
FIG. 9 is a flowchart of a method for maintaining stability to an injury defined by a separation of two bones, according to aspects of the present invention.

FIG. 9 is a flowchart of a method 300 for maintaining stability to an injury by a separation of two bones (e.g., the tibia and fibula bones), the separation being an injured distance greater than a pre-injury distance between the two bones in a first human patient.

In block 302, the method may include delivering the first apparatus 8 for approximation of the two bones in the first human patient having the injury. As discussed herein, the first apparatus 8 may include a first anchor including a proximal end and a distal end configured for insertion into a first hole in a first bone (e.g., the tibia bone) of the two bones. The first anchor may be configured such that there is a distance between the distal end of the first anchor and the medial side of the first bone. That is, the first anchor may not need to be inserted all the way through the first bone. The first apparatus 8 may further include a second anchor including a proximal end and a distal end configured for insertion into a second hole in a second bone (e.g. the fibula bone) of the two bones. The first apparatus 8 may further include a flexible segment extending between the first and second anchors limiting a spacing from the first anchor to the second anchor and configured to adjust a distance between the first and second bones.

In block 304, the method may include maintaining, by the first apparatus 8, a restored distance between the two bones in the first human patient after repetitive dynamic loading (e.g., 1000 cycles, 2000 cycles, 3000 cycles, 4000 cycles, 5000 cycles), the restored distance being approximately equal to the pre-injury distance.

The method may end after block 304, or may optionally include delivering the second apparatus (as discussed herein) for the approximation of the two bones in a second human patient in block 306. The second apparatus may include a flexible segment (e.g., a suture) disposed between a third anchor (e.g., a button disposed on the medial side of the first bone) and a fourth anchor (e.g., a button disposed on the lateral side of the second bone). For example, the second apparatus, delivered into the two bones of the second human patient, may be compared to the first apparatus 8, delivered into the two bones of the first human patient, with respect to how both the first and second apparatus perform in maintaining stability between the respective two bones.

In optional block 308, the method may include maintaining, by the second apparatus, the restored distance between the two bones in the second human patient after the repetitive dynamic loading, the restored distance being approximately equal to the pre-injury distance.

In optional block 310, the method may include decreasing a first change in displacement of the two bones in the first human patient by the first apparatus 8 compared to a second change in displacement of the two bones in the second human patient by the second apparatus.

Figure 10:
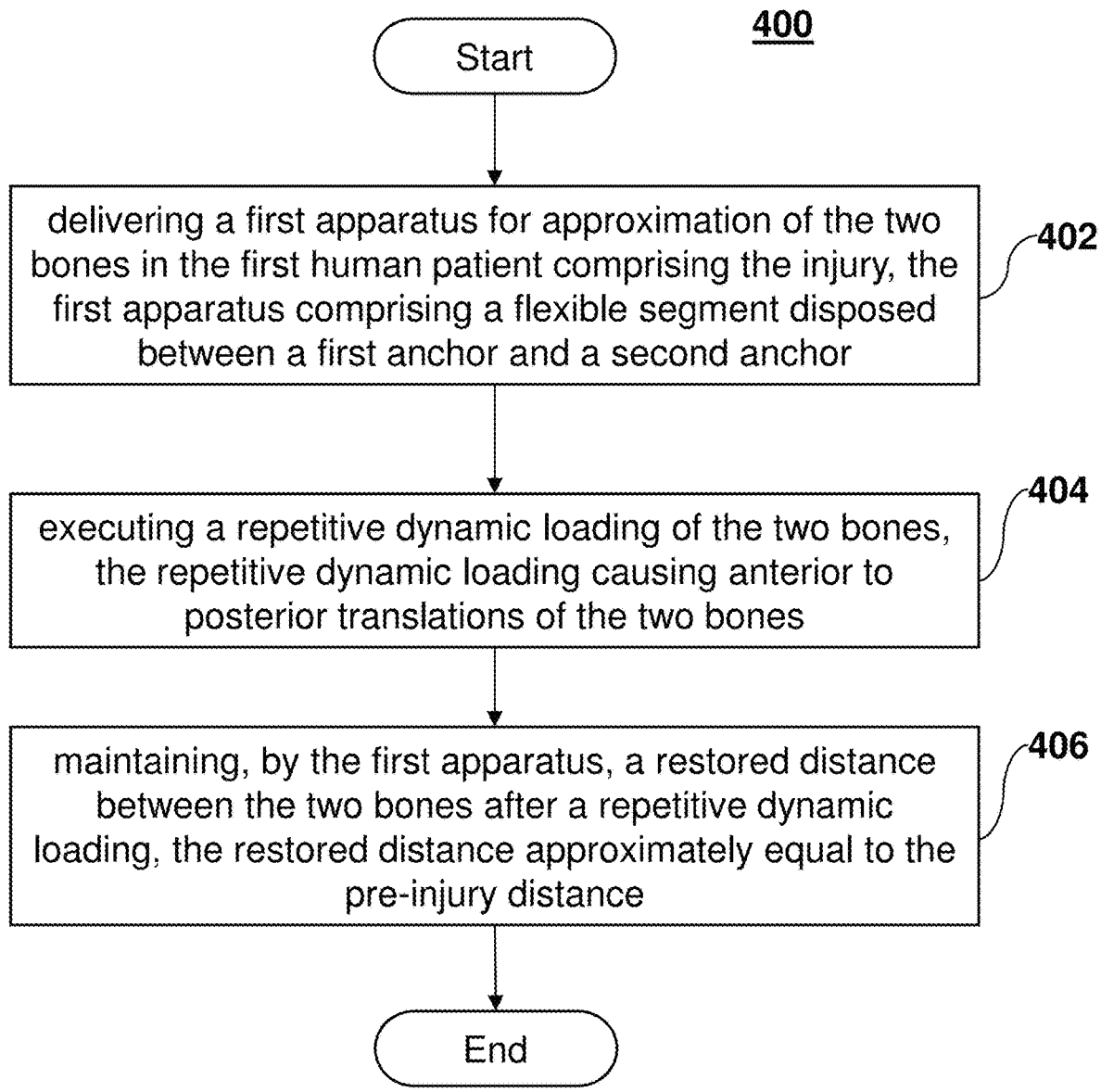
FIG. 10 is a flowchart of a method for maintaining stability to an injury defined by a separation of two bones, according to aspects of the present invention.

FIG. 10 is a flowchart of a method 400 for maintaining stability to an injury by a separation of two bones (e.g., the tibia and fibula bones), the separation being an injured distance greater than a pre-injury distance between the two bones in a first human patient.

In block 402, the method may include delivering a first apparatus 8 for approximation of the two bones in the first human patient having the injury, the first apparatus 8 including a flexible segment disposed between a first anchor and a second anchor.

In block 404, the method may include executing a repetitive dynamic loading of the two bones, the repetitive dynamic loading causing AP translations of the two bones.

In block 406, the method may include maintaining, by the first apparatus 8, a restored distance between the two bones after the repetitive dynamic loading, the restored distance approximately equal to the pre-injury distance.

Figure 11:
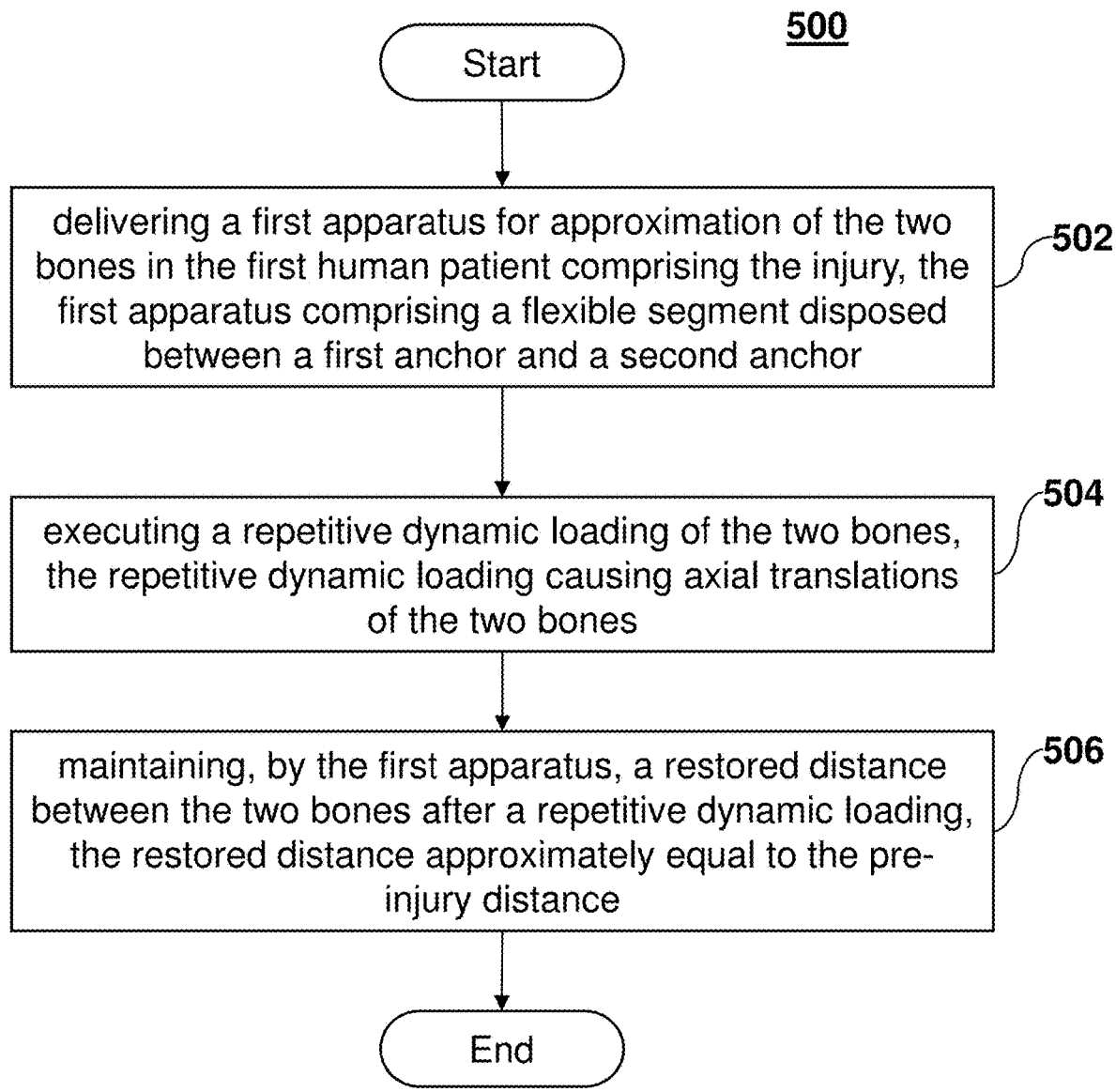
FIG. 11 is a flowchart of a method for maintaining stability to an injury defined by a separation of two bones, according to aspects of the present invention.

FIG. 11 is a flowchart of a method 500 for maintaining stability to an injury by a separation of two bones (e.g., the tibia and fibula bones), the separation being an injured distance greater than a pre-injury distance between the two bones in a first human patient. Method 500 may be the same as or similar to method 400 of FIG. 10, except that method 500 may include the repetitive dynamic loading causing axial translations of the two bones, as opposed to AP translations. The respective descriptions of blocks 502, 504, and 506 may otherwise be the same as or similar to the respective descriptions of blocks 402, 404, and 406, and as such, are not repeated herein for brevity.

In some examples, disclosed systems or methods may involve one or more of the following clauses:

Clause 1: A method of maintaining stability to an injury defined by a separation of two bones, the separation being an injured distance greater than a pre-injury distance between the two bones in a first human patient, the method comprising: delivering a first apparatus for maintaining an approximation of the two bones in the first human patient comprising the injury, the first apparatus comprising a flexible segment disposed between a first anchor and a second anchor; and maintaining, by the first apparatus, a restored distance between the two bones in the first human patient after a repetitive dynamic loading, the restored distance approximately equal to the pre-injury distance.

Clause 2: The method according to clause 1, delivering the first apparatus further comprises maintaining the two bones to a repaired distance measured before the repetitive dynamic loading.

Clause 3: The method according to clause 2, wherein the repetitive dynamic loading causes axial translations of the two bones.

Clause 4: The method according to clause 3, further comprising: maintaining, by the first apparatus, the axial translations of the two bones within a difference of approximately 10.56 percent from the repaired distance after 1000 repetitions.

Clause 5: The method according to clause 4, further comprising: maintaining, by the first apparatus, the difference of approximately 10.56 percent from the repaired distance after 1000 repetitions under a force of up to 1400 newtons (N).

Clause 6: The method according to clause 3, wherein maintaining the axial translations of the two bones after 1000 repetitions comprises a displacement equal to or less than about 0.1 mm.

Clause 7: The method according to clause 3, further comprising: maintaining, by the first apparatus, the axial translations of the two bones within a difference of approximately 10.17 percent from the repaired distance after 2000 repetitions.

Clause 8: The method according to clause 7, further comprising: maintaining, by the first apparatus, the difference of approximately 10.17 percent from the repaired distance after 2000 repetitions under a force of up to 1400 newtons (N).

Clause 9: The method according to clause 7, wherein maintaining the axial translations of the two bones after 2000 repetitions comprises a displacement equal to or less than about 0.1 mm.

Clause 10: The method according to clause 3, further comprising: maintaining, by the first apparatus, the axial translations of the two bones within a difference of approximately 5.57 percent from the repaired distance after 5000 repetitions.

Clause 11: The method according to clause 10, further comprising: maintaining, by the first apparatus, the difference of approximately 5.57 percent from the repaired distance after 5000 repetitions under a force of up to 1400 newtons (N).

Clause 12: The method according to clause 10, wherein maintaining the axial translations of the two bones after 5000 repetitions comprises a displacement equal to or less than about 0.1 mm.

Clause 13: The method according to clause 2, wherein the repetitive dynamic loading causes anterior to posterior translations of the two bones.

Clause 14: The method according to clause 13, further comprising: maintaining, by the first apparatus, the anterior to posterior translations of the two bones within a difference of approximately 20.93 percent from the repaired distance 1000 repetitions.

Clause 15: The method according to clause 14, further comprising: maintaining, by the first apparatus, the difference of approximately 20.93 percent from the repaired distance after 1000 repetitions under a force of up to 1400 newtons (N).

Clause 16: The method according to clause 14, wherein maintaining the anterior to posterior translations of the two bones after 1000 repetitions comprises a displacement equal to or less than about 0.2 mm.

Clause 17: The method according to clause 13, further comprising: maintaining, by the first apparatus, the anterior to posterior translations of the two bones within a difference of approximately 23.71 percent from the repaired distance after 2000 repetitions.

Clause 18: The method according to clause 17, further comprising: maintaining, by the first apparatus, the difference of approximately 23.71 percent from the repaired distance after 2000 repetitions under a force of up to 1400 newtons (N).

Clause 19: The method according to clause 17, wherein maintaining the anterior to posterior translations of the two bones after 2000 repetitions comprises a displacement equal to or less than about 0.2 mm.

Clause 20: The method according to clause 13, further comprising: maintaining, by the first apparatus, the anterior to posterior translations of the two bones within a difference of approximately 20.53 percent from the repaired distance after 5000 repetitions.

Clause 21: The method according to clause 20, further comprising: maintaining, by the first apparatus, the difference of approximately 20.53 percent from the repaired distance after 5000 repetitions under a force of up to 1400 newtons (N).

Clause 22: The method according to clause 20, wherein maintaining the anterior to posterior translations of the two bones after 5000 repetitions comprises a displacement equal to or less than about 0.2 mm.

Clause 23: The method according to clause 1, wherein the first apparatus comprises: the first anchor comprising a proximal end and a distal end configured for insertion into a first hole in a first bone of the two bones, the first anchor being configured such that there is a distance between the distal end of the first anchor and a medial side of the first bone; the second anchor comprising a proximal end and a distal end configured for insertion into a second hole in a second bone of the two bones; and the flexible segment extending between the first and second anchors limiting a spacing from the first anchor to the second anchor and configured to adjust a distance between the first and second bones.

Clause 24: The method according to clause 23, further comprising: delivering a second apparatus for the approximation of the two bones in a second human patient, the second apparatus comprising a second flexible segment disposed between a third anchor and a fourth anchor; maintaining, by the second apparatus, the restored distance between the two bones in the second human patient after the repetitive dynamic loading, the restored distance approximately equal to the pre-injury distance; and decreasing a first change in displacement of the two bones in the first human patient by the first apparatus compared to a second change in displacement of the two bones in the second human patient by the second apparatus.

Clause 25: The method according to clause 24, wherein the repetitive dynamic loading comprises axial translations of the two bones in the respective first and second human patients.

Clause 26: The method according to clause 25, wherein the first change comprises approximately 10.56 percent displacement, and the second change comprises approximately 67.35 percent displacement, thereby decreasing, by the first apparatus, by at least 115.3 percent the displacement of the two bones in the first human patient after 1000 repetitions of axial translations.

Clause 27: The method according to clause 25, wherein the first change comprises approximately 10.17 percent displacement, and the second change comprises approximately 81.99 percent displacement, thereby decreasing, by the first apparatus, by at least 112.1 percent the displacement of the two bones in the first human patient after 2000 repetitions of axial translations.

Clause 28: The method according to clause 25, wherein the first change comprises approximately 5.57 percent displacement, and the second change comprises approximately 116.89 percent displacement, thereby decreasing, by the first apparatus, by at least 104.7 percent, the displacement of the two bones in the first human patient after 5000 repetitions of axial translations.

Clause 29: The method according to clause 24, wherein the repetitive dynamic loading comprises anterior to posterior translations of the two bones in the respective first and second human patients.

Clause 30: The method according to clause 29, wherein the first change comprises approximately 20.93 percent displacement, and the second change comprises approximately 88.91 percent displacement, thereby decreasing, by the first apparatus, by at least 80.3 percent, the displacement of the two bones in the first human patient after 1000 repetitions of anterior to posterior translations.

Clause 31: The method according to clause 29, wherein the first change comprises approximately 23.71 percent displacement, and the second change comprises approximately 112.42 percent displacement, thereby decreasing, by the first apparatus, by at least 82.3 percent, the displacement of the two bones in the first human patient after 2000 repetitions of anterior to posterior translations.

Clause 32: The method according to clause 29, wherein the first change comprises approximately 20.53 percent displacement, and the second change comprises approximately 153.77 percent displacement, thereby decreasing, by the first apparatus, by at least 88.8 percent, the displacement of the two bones in the first human patient after 5000 repetitions of anterior to posterior translations.

Clause 33: A method of maintaining stability to an injury defined by a separation of two bones, the separation being an injured distance greater than a pre-injury distance between the two bones in a first human patient, the method comprising: delivering a first apparatus for approximation of the two bones in the first human patient comprising the injury, wherein the first apparatus comprises: a first anchor configured such that there is a distance between a distal end of the first anchor and a medial side of a first bone of the two bones; a second anchor configured for insertion into a second bone of the two bones; and a flexible segment extending between the first and second anchors and configured to adjust a distance between the first and second bones; and maintaining, by the first apparatus, a restored distance between the two bones after a repetitive dynamic loading, the restored distance approximately equal to the pre-injury distance.

Clause 34: A method of maintaining stability to an injury defined by a separation of two bones, the separation being an injured distance greater than a pre-injury distance between the two bones in a first human patient, the method comprising: delivering a first apparatus for approximation of the two bones in the first human patient comprising the injury, the first apparatus comprising a flexible segment disposed between a first anchor and a second anchor; executing a repetitive dynamic loading of the two bones, the repetitive dynamic loading causing anterior to posterior translations of the two bones; and maintaining, by the first apparatus, a restored distance between the two bones after the repetitive dynamic loading, the restored distance approximately equal to the pre-injury distance.

Clause 35: A method of maintaining stability to an injury defined by a separation of two bones, the separation being an injured distance greater than a pre-injury distance between the two bones in a first human patient, the method comprising: delivering a first apparatus for approximation of the two bones in the first human patient comprising the injury, the first apparatus comprising a flexible segment disposed between a first anchor and a second anchor; executing a repetitive dynamic loading of the two bones, the repetitive dynamic loading causing axial translations of the two bones; and maintaining, by the first apparatus, a restored distance between the two bones after the repetitive dynamic loading, the restored distance approximately equal to the pre-injury distance.

The descriptions contained herein are examples of embodiments of the invention and are not intended in any way to limit the scope of the invention. As described herein, the invention contemplates many variations and modifications of structures and methods, including alternative materials, alternative configurations of component parts, and alternative method steps. Modifications and variations apparent to those having skill in the pertinent art according to the teachings of this disclosure are intended to be within the scope of the claims which follow.

We claim:

1. A method of maintaining stability to an injury defined by a separation of two bones, the separation being an injured distance greater than a pre-injury distance between the two bones in a first human patient, the method comprising:
   delivering a first apparatus configured to achieve semi-rigid and long-term fixation by maintaining an approximation of the two bones in the first human patient comprising the injury, the first apparatus comprising a flexible segment disposed between a first anchor and a second anchor;
   conducting repetitive dynamic loading comprising at least one of axial translations and anterior to posterior translations of the two bones in the first human patient;
   measuring a restored distance between the two bones in the first human patient; and
   maintaining, by the first apparatus, the restored distance between the two bones in the first human patient after the repetitive dynamic loading, the restored distance approximately equal to the pre-injury distance.

2. The method according to claim 1, delivering the first apparatus further comprises maintaining the two bones to a repaired distance measured before the repetitive dynamic loading.

3. The method according to claim 2, wherein the repetitive dynamic loading causes axial translations of the two bones.

4. The method according to claim 3, further comprising:
   maintaining, by the first apparatus, the axial translations of the two bones within a difference of approximately 5.57 percent from the repaired distance after 5000 repetitions.

5. The method according to claim 4, further comprising:
   maintaining, by the first apparatus, the difference of approximately 5.57 percent from the repaired distance after 5000 repetitions under a force of up to 1400 newtons (N).

6. The method according to claim 4, wherein maintaining the axial translations of the two bones after 5000 repetitions comprises a displacement equal to or less than about 0.1 mm.

7. The method according to claim 2, wherein the repetitive dynamic loading causes anterior to posterior translations of the two bones.

8. The method according to claim 7, further comprising:
maintaining, by the first apparatus, the anterior to posterior translations of the two bones within a difference of approximately 20.53 percent from the repaired distance after 5000 repetitions.

9. The method according to claim 8, further comprising:
maintaining, by the first apparatus, the difference of approximately 20.53 percent from the repaired distance after 5000 repetitions under a force of up to 1400 newtons (N).

10. The method according to claim 8, wherein maintaining the anterior to posterior translations of the two bones after 5000 repetitions comprises a displacement equal to or less than about 0.2 mm.

11. The method according to claim 1, wherein the first apparatus comprises:
the first anchor comprising a proximal end and a distal end configured for insertion into a first hole in a first bone of the two bones, the first anchor being configured such that there is a distance between the distal end of the first anchor and a medial side of the first bone;
the second anchor comprising a proximal end and a distal end configured for insertion into a second hole in a second bone of the two bones; and
the flexible segment extending between the first and second anchors limiting a spacing from the first anchor to the second anchor and configured to adjust a distance between the first and second bones.

12. A method of maintaining stability to an injury defined by a separation of two bones, the separation being an injured distance greater than a pre-injury distance between the two bones in a first human patient, the method comprising:
delivering a first apparatus maintaining an approximation of the two bones in the first human patient comprising the injury, the first apparatus comprising a flexible segment disposed between a first anchor and a second anchor;
delivering a second apparatus for the approximation of the two bones in a second human patient, the second apparatus comprising a second flexible segment disposed between a third anchor and a fourth anchor;
conducting repetitive dynamic loading comprising at least one of axial translations and anterior to posterior translations of the two bones in the second human patient;
measuring a restored distance between the two bones in the second human patient;
maintaining, by the second apparatus, the restored distance between the two bones in the second human patient after the repetitive dynamic loading, the restored distance approximately equal to the pre-injury distance; and
decreasing a first change in displacement of the two bones in the first human patient by the first apparatus compared to a second change in displacement of the two bones in the second human patient by the second apparatus.

13. The method according to claim 12, wherein the repetitive dynamic loading comprises axial translations of the two bones in the respective first and second human patients.

14. The method according to claim 13, wherein the first change comprises approximately 10.17 percent displacement, and the second change comprises approximately 81.99 percent displacement, thereby decreasing, by the first apparatus, by at least 112.1 percent the displacement of the two bones in the first human patient after 2000 repetitions of axial translations.

15. The method according to claim 13, wherein the first change comprises approximately 5.57 percent displacement, and the second change comprises approximately 116.89 percent displacement, thereby decreasing, by the first apparatus, by at least 104.7 percent, the displacement of the two bones in the first human patient after 5000 repetitions of axial translations.

16. The method according to claim 12, wherein the repetitive dynamic loading comprises anterior to posterior translations of the two bones in the respective first and second human patients.

17. The method according to claim 16, wherein the first change comprises approximately 23.71 percent displacement, and the second change comprises approximately 112.42 percent displacement, thereby decreasing, by the first apparatus, by at least 82.3 percent, the displacement of the two bones in the first human patient after 2000 repetitions of anterior to posterior translations.

18. The method according to claim 16, wherein the first change comprises approximately 20.53 percent displacement, and the second change comprises approximately 153.77 percent displacement, thereby decreasing, by the first apparatus, by at least 88.8 percent, the displacement of the two bones in the first human patient after 5000 repetitions of anterior to posterior translations.

19. A method of maintaining stability to an injury defined by a separation of two bones, the separation being an injured distance greater than a pre-injury distance between the two bones in a first human patient, the method comprising:
delivering a first apparatus configured to achieve semi-rigid and long-term fixation by maintaining approximation of the two bones in the first human patient comprising the injury, wherein the first apparatus comprises:
a first anchor configured such that there is a distance between a distal end of the first anchor and a medial side of a first bone of the two bones;
a second anchor configured for insertion into a second bone of the two bones; and
a flexible segment extending between the first and second anchors and configured to adjust a distance between the first and second bones;
conducting repetitive dynamic loading comprising at least one of axial translations and anterior to posterior translations of the two bones in the first human patient;
measuring a restored distance between the two bones in the first human patient; and
maintaining, by the first apparatus, the restored distance between the two bones after the repetitive dynamic loading, the restored distance approximately equal to the pre-injury distance.

\* \* \* \* \*